United States Patent [19]

Travers et al.

[11] Patent Number: 5,132,479
[45] Date of Patent: Jul. 21, 1992

[54] MORDENITE-BASED CATALYST CONTAINING AT LEAST ONE METAL FROM GROUP VIII AND ITS USE FOR ISOMERIZING A $C_8$ AROMATIC FRACTION

[75] Inventors: Christine Travers, Rueil Malmaison; Francis Raatz, Acheres; Christian Marcilly, Houilles, all of France

[73] Assignee: Institut Francais Du Petrole, Rueil Malmaison, France

[21] Appl. No.: 786,865

[22] Filed: Nov. 1, 1991

Related U.S. Application Data

[62] Division of Ser. No. 417,143, Oct. 4, 1989, Pat. No. 5,077,254.

[30] Foreign Application Priority Data

Oct. 5, 1988 [FR] France ................... 88 13145

[51] Int. Cl.$^5$ ................................. C07C 5/22
[52] U.S. Cl. ................................. 585/481; 585/477; 585/480; 585/482
[58] Field of Search ................. 585/477, 480, 481, 482

[56] References Cited

U.S. PATENT DOCUMENTS

| | | | |
|---|---|---|---|
| 3,531,243 | 9/1990 | Atken et al. | 502/78 |
| 3,597,155 | 8/1971 | Flanigen | 502/78 |
| 3,673,267 | 6/1972 | Chen et al. | 260/666 P |
| 4,232,181 | 11/1980 | Kiorsky et al. | 585/739 |
| 4,943,546 | 7/1990 | Travers et al. | 502/78 |

Primary Examiner—Patrick P. Garvin
Assistant Examiner—E. D. Irzinski
Attorney, Agent, or Firm—Millen, White & Zelano

[57] ABSTRACT

The invention relates to a catalyst for isomerizing a $C_8$ aromatic fraction containing a mordenite and at least one metal from group VIII of the periodic classification of elements (such as Pt or Pd), characterized in that the mordenite is such that its skeleton Si/Al atomic ratio is between 6 and 10.5, its sodium weight content is below 2000 ppm, its unit cell volume is between 2.73 and 2.78 nm$^3$, its benzene adsorption capacity is between 4 and 10% based on the dry mordenite weight and its 1,3,5-trimethylbenzene adsorption capacity is between 0.5 and 2.5% by weight based on the dry mordenite weight. The invention also relates to the preparation of said mordenite.

9 Claims, No Drawings

MORDENITE-BASED CATALYST CONTAINING AT LEAST ONE METAL FROM GROUP VIII AND ITS USE FOR ISOMERIZING A C₈ AROMATIC FRACTION

This is a division of application Ser. No. 07/417,143, filed Oct. 4, 1989, now U.S. Pat. No. 5,077,254.

The present invention relates to an aluminosilicate-type catalyst incorporating a mordenite, whereof the size of the channels and consequently its geometrical selectivity has been modified in a controlled manner by heat and/or chemical treatments, at least one metal of group VIII of the periodic classification of elements (Handbook of Chemistry and Physics, 6th edition, 1980/1) and optionally a matrix and its use in isomerization reactions of $C_8$ aromatic hydrocarbons.

At present, the catalysts industrially used in these reactions are essentially the zeolite ZSM5, used alone or optionally mixed with other zeolites, such as e.g. mordenite. These catalysts are more particularly described in U.S. Pat. Nos. 4,467,129, 4,482,773 and EP-B-0138617.

The interest of ZSM5 is based on its excellent form selectivity, which leads to a high para-xylene selectivity, due to the size of its channels, which only permit the passage of xylenes and in particular prevent the formation of trimethylbenzene. However, it still has a relatively low activity.

Mordenite is a highly active zeolite, particularly in isomerization reactions of $C_8$ aromatic fractions and is in particular more active than zeolites of structure MFI. However, it is not very selective, the dismutation reaction of the xylenes into trimethylbenzenes and into toluene being very considerable. As a result of the present invention, it is possible to obtain by heat and/or chemical treatments (acid), a mordenite having isomerization performance characteristics (and in particular an isomerization yield) at least equivalent to those of catalysts with a MFI structure and with which consequently the secondary reactions, such as in particular dismutation, are considerably reduced.

The zeolite used in the catalyst according to the present invention is produced from a so-called "small pore" mordenite, whose sodium weight content is generally between 4 and 6.5%, whose skeleton Si/Al atomic ratio is generally between 4.5 and 6.5 and whose unit cell volume is generally between 2.77 and 2.80 nm³ (with 1 nm = $10^{-9}$ m). This mordenite conventionally only adsorbs molecules with a kinetic diameter below approximately $4.4 \times 10^{-10}$ m.

This small pore mordenite firstly undergoes an exchange reaction making it possible to replace the sodium cations by ammonium cations. This exchange is carried out by immersing the mordenite in an ionizable ammonium salt solution, e.g. using ammonium nitrate, which has a molarity generally exceeding 0.5 and at a temperature normally between 20° and 150° C. This exchange stage can be repeated several times and can optionally be followed by one or more washing stages. The sodium weight content of the mordenite obtained in this way is generally below 0.2% and preferably below 0.12%. Its unit cell volume and its Si/Al atomic ratio remains substantially unchanged. Its benzene adsorption capacity is approximately 1% by weight based on the dry mordenite weight and it only has a very limited trimethylbenzene adsorption. Its water weight content is between 5 and 40% and preferably between 10 and 30%.

According to the invention, the mordenite obtained with the water weight content indicated hereinbefore, must undergo various treatments and in particular either at least one calcination under a dry air stream, which may or may not be followed by at least one acid action, or at least one direct acid action, particularly to at least partly clear or unblock its structure.

The term calcination under a dry air stream is understood to mean a heat treatment, performed under very precise temperature, air water content and air flow rate conditions, which makes it possible to leave the steam given off by the solid sufficiently in contact with said solid for it to act on the structure and to remove the aluminium from the skeleton to a greater or lesser extent as a function of the calcination temperature used. This aluminium removal from the skeleton by continuous elimination of the aluminum atoms in the tetrahedral position leads, in the case of the small pore mordenite used in the invention, to an unblocking of the porosity which can be controlled by controlling the calcination temperature.

The calcination conditions used in preferred manner in the present invention are a water weight content in the air (prior to its contact with the solid) below 1% and preferably below 300 ppm, an air flow rate between 0.5 and 10 liters/hour/gramme of solid and preferably between 1 and 5 liters/hour/gramme of solid (l/h/g), a calcination temperature between approximately 450° and approximately 650° C. and preferably between approximately 450° and approximately 580° C. and a temperature rise rate between 2° and 8° C./minute and preferably between 3° and 6° C./minute.

The final calcination temperature will generally be maintained for approximately 0.5 to approximately 5 hours and preferably for approximately 1 to approximately 4 hours.

The thermal calcination treatment under a dry air stream can optionally be followed by at least one (gentle) acid action operation making it possible to eliminate the aluminium ions in the octahedral position without affecting the aluminium ions of the skeleton. For this purpose, following calcination, the solid is heated in a mineral or organic acid solution, such as e.g. hydrochloric or nitric acid, with a normality normally below 2N and preferably below 0.5N, at a temperature below approximately 100° C. and preferably below approximately 60° C. This generally lasts for approximately 4 hours and with a $H_s^+/Al_z$ ratio between 8.5 and 11.5 and preferably equal to 10, in which $H_s^+$ is the number of proton moles in solution and $Al_z$ is the number of aluminium cation moles in the mordenite.

The mordenite according to the invention can also be obtained by at least one direct acid action process, which consists of heating, to a temperature exceeding approximately 70° C. and preferably exceeding approximately 85° C., the zeolite following the cationic exchange stage (and optionally washing) in an organic or mineral acid solution, such as e.g. hydrochloric or nitric acid, with a normality conventionally between 0.1 and 5N and preferably between 0.2 and 3N, for in general approximately 2 hours, with a $H_s^+/Al_z$ ratio between 5 and 20 and preferably between 8 and 15, in which $H_s^+$ is the number of proton moles in the solution and $Al_z$ the number of aluminium cation moles in the mordenite. So there is an extraction of the aluminum cations both in the tetrahedral and octahedral positions and consequently an unblocking of the porosity which increases with the intensity of the acid action.

The mordenite obtained by one of the preceding treatments has a unit cell volume between 2.73 and 2.78 nm$^3$. Its skeleton Si/Al atomic ratio is between 6 and 10.5 and preferably between 6 and 9.5. The sodium weight ratio of said mordenite is generally below 2000 ppm and is preferably below 1000 ppm. Its benzene adsorption capacity varies from 4 to 10% and preferably 5 to 9% by weight based on the dry mordenite weight and its 1,3,5-trimethylbenzene adsorption capacity is 0.5 to 2.5%, preferably 0.7 to 2% by weight based on the dry mordenite weight.

The mordenites contained in the catalysts according to the invention consequently have the special feature of being able to adsorb relatively large benzene quantities, but of only very slightly adsorbing 1,3,5-trimethylbenzene, which is a product formed during the undesirable dismutation reaction of xylenes. Their adsorption capacities are in general determined by gravimetry, e.g. in accordance with the following method: A sample of the mordenite is previously desorbed at 300° C. under $10^{-4}$ Torr ($133.32 \times 10^{-4}$ Pa), adsorption then being carried out for at least 4 hours under the following conditions:

for benzene adsorption:
T=30° C.
P=28 Torr (3733 Pa)
P/Ps=0.25
for the 1,3,5-trimethylbenzene adsorption:
T=50° C.
P=3 Torr (400 Pa)
P/Ps=0.26 in which Ps represents the saturated steam pressure at the temperature of the experiment. The adsorbed volumes are calculated on the basis of the density of the adsorbate in liquid form at the adsorption temperature: $d_o=0.868$ for benzene and $d_o=0.839$ for 1,3,5-trimethylbenzene.

The other characteristics can be measured by the following methods:

the skeleton Si/Al atomic ratios are determined by infrared spectrometry and the sodium contents by atomic adsorption;

the unit cell volume is determined by X-defraction, the mordenite sample being prepared in an identical way to the operating procedure of ASTM D Standard 3942 80 for faujasite.

The thus modified mordenite can then be subjected as it is to the deposition of at least one group VIII metal, preferably chosen from the group formed by platinum and palladium, and shaped by all known procedures. It can in particular be mixed with a generally amorphous matrix, e.g. a humid alumina gel powder. The mixture is then shaped, e.g. by extrusion through a die. The mordenite content of the support (mordinite+matrix) obtained in this way is generally between approximately 0.5 and 99.99% and advantageously between 40 and 90% by weight, based on the support. It is more particularly between approximately 60 and 85% by weight, based on the support. The matrix content of the catalyst is advantageously between approximately 10 and 60% and preferably between approximately 15 and 40% by weight, based on the support (mordenite+matrix).

The shaping can be carried out with matrixes other than alumina, such as e.g. magnesia, silica-alumina, natural clays (kaolin, bentonite) and by methods other than extrusion, such as pellet or dragée formation.

The hydrogenating metal of group VIII, preferably Pt and/or Pd, is then deposited on the support by any known process permitting the deposition of metal on mordenite. It is possible to use the cation exchange method with competition, in which the competing agent is preferably ammonium nitrate, the competition ratio being at least equal to approximately 50 and advantageously approximately 50 to 200. In the case of platinum or palladium, it is standard practice to use a tetrammine complex of platinum or a tetrammine complex of palladium. The latter would then be substantially entirely deposited on the mordenite. This cation exchange method can also be used for directly depositing the metal on the mordenite powder before its possible mixing with a matrix.

The deposition of the metal (or metals) is generally followed by a calcination under air or oxygen, usually at between 300° and 600° C. for 0.5 to 10 hours and preferably at 350° to 550° C. for 1 to 4 hours. It is then possible to carry out reduction under hydrogen, generally at a temperature between 300° and 600° C. for 1 to 10 hours and preferably 350° to 550° C. for 2 to 5 hours. The content of the metal of group VIII (Pt and/or Pd) deposited on the catalyst and obtained following the exchange is between 0.05 and 1.5% and preferably between 0.1 and 1% by weight, based on the total catalyst.

The platinum or palladium may also be deposited on the alumina binder and not directly on the mordenite, before or after the shaping stage, by carrying out an anion exchange with hexachloroplatinic acid, hexachloropalladic acid and/or palladium chloride in the presence of a competing agent, e.g. hydrochloric acid. Prior to the deposition of the platinum and/or palladium, as hereinbefore, the catalyst undergoes a calcination, generally at between 300° and 600° C. and is then reduced under hydrogen in the aforementioned manner.

The bifunctional catalyst obtained by the above procedures can be used in the isomerization reactions of a C$_8$ aromatic fraction, e.g. comprising either solely a mixture of xylenes, or a mixture of xylenes and ethyl benzene. The isomerization of the alkyl aromatics and in particular xylenes has a considerable commerical importance. Generally para-xylene is the most sought product, because it is used as an intermediate in the production of polyester fibres. Preference is given to the production of para-xylene by isomerizing meta-xylene, which can be obtained by the isomerization of ortho-xylene. The ethyl benzene, which is difficult to separate by distillation from the mixture of xylenes (the boiling points of the different compounds being very close to one another), very frequently occurs in the isomerization charge of the C$_8$ aromatics.

The operating conditions for the isomerization process are generally as follows:

temperature between 240° and 600° C., preferably between 350° and 510° C, pressure between 0.5 and 100 bars, preferably between 2 and 30 bars, space velocity (pph), in charge mass per catalyst charge unit and per hour, between 0.5 and 200 and preferably between 5 and 100, molar ratio of hydrogen to hydrocarbons in the charge (H$_2$/HC) between 0.5 and 12 and preferably between 2 and 6.

The following examples illustrate the invention without limiting its scope. They are given for a charge formed from 75% ortho-xylene and 25% ethyl benzene (by weight).

EXAMPLE 1

Catalyst A according to the invention

The starting substance is a small pore mordenite called Alite 150 of the Societe Chimique de la Grande Paroisse. Its chemical formula in the anhydrous state is Na $AlO_2(SiO_2)_{5.5}$ and its benzene adsorption capacity is 1% by weight, based on the dry solid weight (unit cell volume: 2.79 nm$^3$; sodium content: 5.3% by weight; kinetic diameter of adsorbed molecules: $3.8 \times 10^{-10}$m). 50 g of this poweder are immersed in a 2M ammonium nitrate solution and the solution heated to 95° C. for two hours.

The volume of the ammonium nitrate solution used is equal to four times the dry zeolite weight (vol/wt=4). This cation exchange operation is repeated three times. After the third exchange, the product is washed with water at 20° C. for 20 minutes with a vol/wt ratio of 4. The sodium content, expressed as a weight percentage based on the dry solid weight, passes from 5.5 to 0.1%. The product is then filtered and undergoes calcination under a dry air stream, whose water weight content is below 300 ppm, at approximately 550° C. and for 2 hours.

For this purpose, 2 g of powder (mordenite with a water weight content of approximately 25%) in the form of ammonium are fed into a diameter 30 mm quartz reactor. The powder bed formed is traversed by a dry air flow of 2 l/h. The temperature rise rate is 4.2° C./min. Once the temperature reaches 550° C., the temperature is maintained at this level for 2 hours.

The thus obtained mordenite has a skeleton Si/Al atomic ratio of 7.5. Its sodium weight content is 1000 ppm. Its unit mesh volume is 2.76 nm$^3$. Its benzene adsorption capacity is 8% by weight, based on the dry mordenite weight and its 1,3,5-trimethylbenzene adsorption capacity is 1.8% by weight, based on the dry mordenite weight.

Intimate mixing then takes place between said mordenite and the alumina, on which has been dispersed 0.3% by weight of platinum, the support constituted by the mordenite-alumina mixture containing 40% by weight alumina. The platinum weight content of the final catalyst A is therefore 0.12%.

The thus produced catalyst is shaped by pelletizing, calcined under air up to 500° C. for 2 hours and reduced under hydrogen at 500° C. for 3 hours.

Catalyst A is then tested in the isomerization of the mixture of orthoxylene (75% by weight) and ethylbenzene (25% by weight), at 420° C., under 15 bars and with a space velocity (pph) of 50 (hour)$^{-1}$ and a molar ratio of hydrogen to hydrocarbon ($H_2/HC$) of approximately 4.

The performance characteristics of catalyst A (and catalyst prepared in the following examples), given in Table I, are defined by:

$$\text{o-xylene conversion (\%)} = \frac{\text{o-xylene mass in the charge} - \text{o-xylene mass in the formulation}}{\text{o-xylene mass in the charge}} \times 100$$

$$\text{isomerization selectivity (\%)} = \frac{\text{m-xylene mass} + \text{p-xylene mass}}{\text{mass of products}} \times 100$$

$$\text{isomerization yield (\%)} = \frac{\text{conversion} \times \text{selectivity}}{100}$$

$$\text{dismutation selectivity (\%)} = \frac{\text{trimethylbenzene mass} + \text{toluene mass} + \text{benzene mass}}{\text{mass of products}} \times 100$$

$$\text{cracking selectivity (\%)} = \frac{\text{mass of C1 to C4 gases}}{\text{mass of products}} \times 100$$

EXAMPLE 2

Catalyst B according to the invention

Catalyst B differs from catalyst A prepared in Example 1 in that following the calcination stage under a dry air stream, the mordenite undergoes gentle acid action consisting of heating the mordenite in a 0.2N hydrochloric acid solution at 50° C. for 4 hours with an approximate $H_s^+/Al_z$ ratio of 10.

The thus obtained mordenite has a skeleton Si/Al atomic ratio of 7.5. Its sodium weight content is below 300 ppm. Its unit cell volume is 2.76 nm$^3$. Its benzene adsorption capacity is 8% by weight, based on the dry mordenite weight and its 1,3,5-trimethylbenzene adsorption capacity is 1.8% by weight, based on the dry mordenite weight.

The stages of mordenite-alumina mixing, platinum dispersion, shaping, calcination, catalyst reduction and isomerization test conditions are the same as those described for Example 1. The performance characteristics of the catalyst B are given in Table I.

EXAMPLE 3

Catalyst C according to the invention

Catalyst C differs from catalyst A prepared in Example 1 in that following the third cation exchange (and water washing), the solid directly undergoes acid action: It is refluxed in a 0.3N hydrochloric acid solution at 90° C. for 2 hours with an approximate $H_s^+/Al_z$ ratio of 10.

The thus obtained mordenite has a skeleton Si/Al atomic ratio of 7.6. Its sodium weight content is below 300 ppm. Its unit cell volume is 2.76 nm$^3$. Its benzene adsorption capacity is 8.1% by weight, based on the dry mordenite weight and its 1,3,5-trimethylbenzene adsorption capacity is 1.75% by weight, based on the dry mordenite weight.

The stages of mordenite-alumina mixing, platinum dispersion, shaping, calcination, catalyst reduction and the isomerization test conditions are the same as those described in Example 1. The performance characteristics of the catalyst C are given in Table I.

EXAMPLE 4

Catalyst D, not according to the invention

Catalyst D contains a zeolite of structure MFI, synthesized in a fluoride medium. This zeolite has a skeleton Si/Al atomic ratio of 250. Its sodium weight content is 50 ppm. Its unit cell volume is 5.36 nm$^3$. Its benzene adsorption capacity is 9.5% by weight, based on the dry zeolite weight and its 1,3,5-trimethylbenzene adsorption capacity is 1.5% by weight, based on the dry zeolite weight.

The stages of zeolite-alumina mixing, platinum dispersion, shaping, calcination, catalyst reduction and the isomerization test conditions are identical to those described in Example 1, but with a pph of 30 (hours)$^{-1}$.

The performance characteristics of catalyst D are given in Table I.

EXAMPLE 5

Catalyst E, not according to the invention

Catalyst E (described in European patent application EP-A-196965) differs from catalyst A prepared in Example 1 in that after the third cation exchange (and water washing), the solid is filtered and undergoes calcination in a confined atmosphere (self-steaming) at 600° C. and for 2 hours (the calcination atmosphere containing at least 5% steam). This is followed by acid action, the solid being refluxed in a 0.6N hydrochloric acid solution at 90° C. for 2 hours, with a vol/wt ratio of 8, in which vol is the volume of the hydrochloric acid solution and wt the dry mordenite weight. The product is then filtered, washed with 0.1N hydrochloric acid and then with water.

The thus obtained mordenite has a skeleton Si/Al atomic ratio of 12. Its sodium weight content is approximately 300 ppm. Its unit cell volume is 2.75 nm$^3$. Its benzene adsorption capacity is 9.6% by weight, based on the dry mordenite weight and its 1,3,5-trimethylbenzene adsorption capacity is 8% by weight, based on the dry mordenite weight. This means that the small pore mordenite is completely unblocked and is equivalent to a large pore mordenite from the adsorption capacity standpoint.

The stages of mordenite-alumina mixing, platinum dispersion, shaping, calcination, catalyst reduction and the isomerization test conditions are identical to those described in Example 1. The performance characteristics of catalyst E appear in Table 1.

Catalyst A, B and C according to the invention have better performance characteristics than the prior art catalysts D and E. The isomerization yield of catalysts A, B and C is higher than that of catalysts D and E. Indeed catalyst D is much less active than catalysts A, B and C and catalyst E has a very limited selectivity.

TABLE I

| | CATALYST | | | | |
|---|---|---|---|---|---|
| | A | B | C | D | E |
| | Example | | | | |
| | 1 | 2 | 3 | 4 | 5 |
| pph (h$^{-1}$) | 50 | 50 | 50 | 30 | 50 |
| o-xylene conversion (%) | 58.0 | 57.5 | 58.0 | 50.0 | 79.5 |
| isomerization selectivity (%) | 80.0 | 81.2 | 79.5 | 91.5 | 27.0 |
| isomerization yield (%) | 46.4 | 46.7 | 46.1 | 45.7 | 21.5 |
| dismutation selectivity (%) | 6.5 | 6.6 | 6.4 | 5.5 | 55.0 |
| cracking selectivity (%) | 1.5 | 1.5 | 1.6 | 0.8 | 1.7 |

We claim:

1. A process for isomerization of a C$_8$-aromatic fraction, comprising subjecting said fraction to isomerization conditions in the presence of a catalyst comprising a mordenite and at least one metal from group VIII of the periodic classification of elements, wherein said mordenite is such that its skeleton Si/Al atomic ratio is between 6 and 10.5, its sodium weight content is below 2000 ppm, its unit mesh volume is between 2.73 and 2.78 nm$^3$, its benzene adsorption capacity is between 4 and 10% by weight, based on the dry mordenite weight and its 1,3,5-trimethylbenzene adsorption capacity is between 0.5 and 2.5% by weight, based on the dry mordenite weight.

2. A process according to claim 1, wherein said mordenite is such that its benzene adsorption capacity is between 5 and 9% by weight, based on the dry mordenite weight and its 1,3,5-trimethylbenzene adsorption capacity is between 0.7 and 2% by weight, based on the dry mordenite weight.

3. A process according to claim 1, wherein said mordenite is such that its skeleton Si/Al atomic ratio is between 6 and 9.5 and its sodium weight content is below 1000 ppm.

4. A process according to claim 1 in which the metal is platinum or palladium.

5. A process according to claim 1, further comprising a matrix.

6. A process according to claim 1, wherein the catalyst is prepared from a small pore mordenite having a skeleton Si/Al atomic ratio between 4.5 and 6.5, a sodium weight content between 4 and 6.5%, a unit cell volume between 2.77 and 2.80 nm$^3$, said small pore mordenite only adsorbing molecules with a kinetic diameter below approximately $4.4 \times 10^{-10}$ m, the process comprising:
   (a) at least one exchange of the sodium cations of the small pore mordenite by ammonium cations,
   (b) a solid obtained in stage a) is subjected to a calcination under a dry air stream, having a water weight content below 1%, under an air flow rate between 1 and 5 liters/hour/gram of solid, at a temperature between approximately 450° and 650° C., with a temperature rise rate between 2° and 8° C./minute, the final calcination temperature being maintained for approximately 0.5 to approximately 5 hours.

7. A process according to claim 6 in which a solid obtained in stage (b) is heated in a mineral or organic acid solution with a normality below 0.5N, at a temperature below approximately 60° C., with a H$_s^+$/Al$_z$ ratio between 8.5 and 11.5, in which H$_s^+$ is the number of proton moles in solution and Al$_z$ the number of aluminium cation moles in the mordenite.

8. A process according to claim 1, wherein the catalyst is prepared from a small pore mordenite having a skeleton Si/Al atomic ratio is between 4.5 and 6.5, a sodium weight content is between 4 and 6.5%, a unit cell volume is between 2.77 and 2.80 nm$^3$, said small pore mordenite only adsorbing molecules with a kinetic diameter below approximately $4.4 \times 10^{-10}$ m, the process comprising:
   (a) at least one exchange of the sodium cations of the small pore mordenite by ammonium cations,
   (b) a solid obtained in stage (a) is heated to a temperature above approximately 85° C. in a solution of a mineral or organic acid with a normality between 0.2 and 3N, with a H$_s^+$/Al$_z$ ratio between 8 and 15, in which H$_s^+$ is the number of proton moles in the solution and Al$_z$ the number of aluminium cation moles in the mordenite.

9. A process according to claim 5, wherein the matrix is alumina.

* * * * *